(12) United States Patent
Chen et al.

(10) Patent No.: US 7,535,563 B1
(45) Date of Patent: May 19, 2009

(54) SYSTEMS CONFIGURED TO INSPECT A SPECIMEN

(75) Inventors: Grace Hsiu-Ling Chen, San Jose, CA (US); Tao-Yi Fu, Fremont, CA (US); Jamie Sullivan, Eugene, OR (US); Shing Lee, Fremont, CA (US); Greg Kirk, Pleasanton, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 268 days.

(21) Appl. No.: 11/464,567

(22) Filed: Aug. 15, 2006

(51) Int. Cl.
*G01N 21/00* (2006.01)

(52) U.S. Cl. .................. 356/237.5; 356/237.1

(58) Field of Classification Search ... 356/237.1–241.6, 356/426–431, 600–640
See application file for complete search history.

(56) References Cited

U.S. PATENT DOCUMENTS

| | | | |
|---|---|---|---|
| 5,276,498 A | 1/1994 | Galbraith et al. | |
| 5,327,286 A * | 7/1994 | Sampsell et al. | 359/561 |
| 5,506,676 A * | 4/1996 | Hendler et al. | 356/237.1 |
| 5,587,832 A * | 12/1996 | Krause | 359/385 |
| 5,966,212 A | 10/1999 | Hendler et al. | |
| 6,288,780 B1 * | 9/2001 | Fairley et al. | 356/237.1 |
| 6,392,793 B1 | 5/2002 | Chuang et al. | |
| 6,566,627 B2 * | 5/2003 | Brandinger et al. | 219/121.69 |
| 6,686,602 B2 * | 2/2004 | Some | 250/559.45 |
| 6,686,994 B2 | 2/2004 | Wilk et al. | |
| 6,686,995 B2 | 2/2004 | Wilk et al. | |
| 6,882,417 B2 * | 4/2005 | Goldberg et al. | 356/237.4 |
| 7,199,874 B2 * | 4/2007 | Bevis et al. | 356/237.5 |
| 7,330,265 B2 * | 2/2008 | Kurosawa et al. | 356/445 |
| 2005/0286045 A1 * | 12/2005 | Volfman et al. | 356/237.1 |
| 2006/0007436 A1 | 1/2006 | Kurosawa et al. | |
| 2006/0012781 A1 | 1/2006 | Fradkin et al. | |

* cited by examiner

*Primary Examiner*—L. G. Lauchman
*Assistant Examiner*—Jarreas C Underwood
(74) *Attorney, Agent, or Firm*—Baker & McKenzie LLP (57) ABSTRACT

Systems configured to inspect a specimen are provided. One system includes an illumination subsystem configured to illuminate a two-dimensional field of view on the specimen. The system also includes a collection subsystem configured to collect light scattered from the specimen. In addition, the system includes an array of micro-mirrors configured to reflect a two-dimensional pattern of light diffracted from periodic structures on the specimen out of the optical path of the system without reflecting light across an entire dimension of the array out of the optical path. The system further includes a detection subsystem configured to generate output responsive to light reflected by the array into the optical path. The output can be used to detect defects on the specimen. In one embodiment, the system includes an optical element configured to increase the uniformity of the wavefront of the light reflected by the array into the optical path.

19 Claims, 4 Drawing Sheets

SYSTEMS CONFIGURED TO INSPECT A SPECIMEN

BACKGROUND OF THE INVENTION

1. Field of the Invention

This invention generally relates to systems configured to inspect a specimen. Certain embodiments relate to a system that includes an array of micro-mirrors configured to reflect light diffracted from periodic structures on the specimen out of the optical path of the system.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Many different types of inspection tools have been developed for the inspection of semiconductor wafers. Defect inspection is currently performed using techniques such as bright field (BF) imaging, dark field (DF) imaging, and scattering. The type of inspection tool that is used for inspecting semiconductor wafers may be selected based on, for example, characteristics of the defects of interest and characteristics of the wafers that will be inspected. For example, some inspection tools are designed to inspect unpatterned semiconductor wafers or patterned semiconductor wafers.

Inspection tools for unpatterned wafers are generally not capable of inspecting patterned wafers for a number of reasons. For example, many unpatterned wafer inspection tools are configured such that all of the light collected by a lens or another collector is directed to a single detector that generates a single output signal representative of all of the collected light. Therefore, light scattered from patterns or other features on the specimen will be combined with other scattered light. As such, light scattered from patterns or other features on the wafer cannot be detected separately from other scattered light thereby hindering, if not preventing, defect detection.

Patterned wafer inspection is of particular interest and importance to the semiconductor industry because processed semiconductor wafers usually have a pattern of features formed thereon. Although inspection of unpatterned wafers, or "monitor wafers," which have been run through a process tool, may be used as a gauge for the number and types of defects that may be found on patterned wafers, or "product wafers," defects detected on monitor wafers do not always accurately reflect the defects that are detected on patterned wafers after the same process in the same process tool. Inspection of patterned wafers is, therefore, important to accurately detect defects that may have been formed on the wafer during, or as a result of, processing. Therefore, inspecting patterned wafers or product wafers may provide more accurate monitoring and control of processes and process tools than inspection of monitor wafers.

Many inspection tools have been developed for patterned wafer inspection. Some patterned wafer inspection tools utilize spatial filters to separate light scattered from patterned features from other scattered light such that the other scattered light may be separately detected. Since the light scattered from patterned features depends on various characteristics of the patterned features such as lateral dimension and period, the design of the spatial filter also depends on such characteristics of the patterned features. As a result, the spatial filter must be designed based on known or determined characteristics of the patterned features and must vary as different patterned features are being inspected.

One type of spatial filter that may be used as described above is a Fourier filter. Fourier filters are relatively useful for filtering light from repetitive patterns such as memory arrays formed on a wafer. At least two previous methods have been used for Fourier filtering. One method is a mechanical method. This method utilizes mechanical rods or other mechanical devices to block the diffraction pattern generated by array structures so that the energy from the array region is removed from the optical path of the inspection system. Another method is a liquid crystal method. This method utilizes a one-dimensional or two-dimensional liquid crystal device to block the diffraction pattern generated by array structures so that the energy from the array region is removed from the optical path of the inspection system.

Although the above Fourier filtering methods have been relatively widely used, these methods do have a number of significant disadvantages. For example, the mechanical method has a number of disadvantages, particularly for flood illumination based systems. In particular, the diffraction peaks for flood illumination based systems are dots. Mechanical rods, therefore, block excessive amounts of light in such systems thereby reducing the overall defect signals. In addition, the mechanical method induces significantly more Fourier filter ringing that causes periphery energy leakage in output generated during inspection of the array region thereby reducing defect sensitivities in the array region. In particular, Fourier filters in the form of periodic blocking bars can diffract light into undesirable directions, which is commonly referred to as ringing or side lobes, thereby degrading the imaging quality. Therefore, the Fourier filter can produce significant distortion at the image plane, which adversely affects the ability of the inspection system to detect defects on the wafer with high accuracy. Furthermore, since the rods must have a relatively large diameter in order to be structurally sound, only a limited number of rods can be used. Otherwise, the entire plane would be blocked by the rods.

Currently used liquid crystal Fourier filter devices are programmable and capable of filtering out diffraction dots in a two-dimensional manner. However, there are several factors that make the liquid crystal devices inappropriate for flood illumination based systems. For example, the use of a liquid crystal device as a Fourier filter utilizes the principle of light scattering. For a flood illumination based system, the light scattering significantly alters the wavefront of the system thereby causing severe degradation to the image quality. In addition, most liquid crystal material has a damage threshold at a wavelength of approximately 300 nm thereby making liquid crystal devices less than ideal for use in deep ultraviolet (DUV) based systems (i.e., systems that operate at wavelength(s) less than about 300 nm).

Accordingly, it would be advantageous to develop a system configured to inspect a specimen that includes a two-dimensional programmable Fourier filter suitable for flood illuminated dark field wafer inspection systems, which does not block excessive amounts of light such that the overall defect signals are not reduced, does not induce significant Fourier filter ringing and periphery energy leakage, does not significantly alter the wavefront of the system, does not cause degradation of the image, is structurally sound, and is suitable for use at DUV and other wavelengths.

SUMMARY OF THE INVENTION

The following description of various system embodiments is not to be construed in any way as limiting the subject matter of the appended claims.

One embodiment relates to a system configured to inspect a specimen. The system includes an illumination subsystem configured to illuminate a two-dimensional field of view (FOV) on the specimen. The system also includes a collection subsystem configured to collect light scattered from the specimen. In addition, the system includes an array of micro-mirrors configured to reflect a two-dimensional pattern of light diffracted from periodic structures on the specimen out of the optical path of the system without reflecting light across an entire dimension of the array out of the optical path. The system further includes a detection subsystem configured to generate output responsive to light reflected by the array into the optical path. The output can be used to detect defects on the specimen.

In one embodiment, the array is positioned at a Fourier plane of the collection subsystem. In another embodiment, the system includes an optical element configured to increase the uniformity of the wavefront of the light reflected by the array into the optical path.

In an embodiment, the FOV has an approximately elliptical shape on the specimen. In another embodiment, a dimension of the FOV in a y direction is larger than a dimension of the FOV in an x direction. In one such embodiment, a dimension of the micro-mirrors parallel to the y direction is larger than a dimension of the micro-mirrors parallel to the x direction. In another such embodiment, a dimension of the micro-mirrors parallel to the y direction is larger than a dimension of the micro-mirrors parallel to the x direction, and the system includes an optical element configured to increase the uniformity of the wavefront of the light reflected by the array into the optical path. In an additional such embodiment, a fill factor of the micro-mirrors parallel to the y direction is larger than a fill factor of the micro-mirrors parallel to the x direction. In a further such embodiment, a dimension of the micro-mirrors parallel to the y direction is larger than a dimension of the micro-mirrors parallel to the x direction, and the array is configured such that the micro-mirrors are tilted in the x direction.

In some embodiments, the array is configured to reflect approximately all ringing energy due to dead space in the array outside of the FOV of the detection subsystem. In one embodiment, a dimension of the FOV in a y direction is larger than a dimension of the FOV in an x direction, a dimension of the micro-mirrors parallel to the y direction is larger than a dimension of the micro-mirrors parallel to the x direction, and the dimension of the micro-mirrors in the x direction is selected such that the array reflects approximately all dead space ringing energy outside of the FOV of the detection subsystem in the x direction. In another embodiment, the array is configured such that the array does not cause degradation of the output.

In one embodiment, the array is configured such that the micro-mirrors can be independently tilted. In another embodiment, the array is configured such that the micro-mirrors can be independently tilted based on the periodic structures formed on the specimen. Each of the embodiments described above may be further configured as described herein.

Another embodiment relates to a system configured to inspect a specimen. This system includes a collection subsystem configured to collect light scattered from the specimen. The system also includes an array of micro-mirrors configured to reflect light diffracted from periodic structures on the specimen out of the optical path of the system. In addition, the system includes an optical element configured to increase the uniformity of the wavefront of light reflected by the array into the optical path of the system. The system further includes a detection subsystem configured to generate output responsive to light exiting the optical element. The output can be used to detect defects on the specimen.

In one embodiment, a dimension of the FOV of the system in a y direction is larger than a dimension of the FOV in an x direction. In one such embodiment, a dimension of the micro-mirrors parallel to the y direction is larger than a dimension of the micro-mirrors parallel to the x direction. In a further embodiment, the array is configured to reflect approximately all ringing energy due to dead space in the array outside of the FOV of the detection subsystem. In an additional embodiment, the array is configured such that the array does not cause degradation of the output. Each of the embodiments described above may be further configured as described herein.

An additional embodiment relates to a system configured to inspect a specimen. The system includes an illumination subsystem configured to illuminate a two-dimensional FOV on the specimen. A dimension of the FOV in a y direction is larger than a dimension of the FOV in an x direction. The system also includes a collection subsystem configured to collect light scattered from the specimen. In addition, the system includes an array of micro-mirrors configured to reflect light diffracted from periodic structures on the specimen out of the optical path of the system. A dimension of the micro-mirrors parallel to the y direction is larger than a dimension of the micro-mirrors parallel to the x direction. The system further includes a detection subsystem configured to generate output responsive to light reflected by the array into the optical path. The output can be used to detect defects on the specimen.

In one embodiment, a fill factor of the micro-mirrors parallel to the y direction is larger than a fill factor of the micro-mirrors parallel to the x direction. In another embodiment, the array is configured such that the micro-mirrors are tilted in the x direction. In an additional embodiment, the array is configured to reflect approximately all ringing energy due to dead space in the array outside of the FOV of the detection subsystem. In a further embodiment, the array is configured such that the array does not cause degradation of the output. Each of the embodiments described above may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features or periodic structures. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
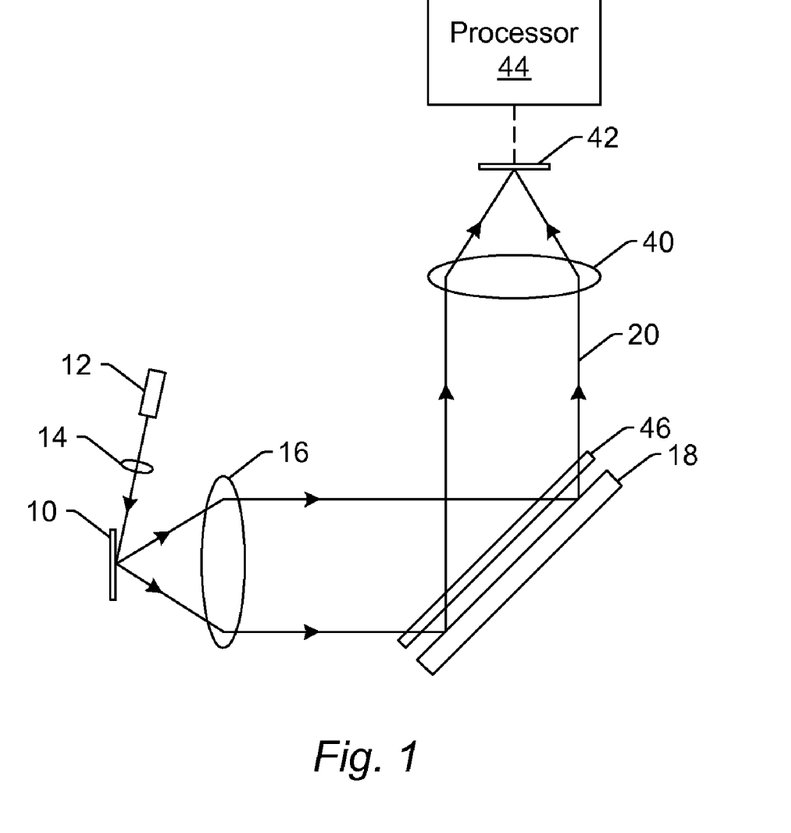
FIG. 1 is a schematic diagram illustrating a side view of one embodiment of a system configured to inspect a specimen.

FIG. 1 illustrates one embodiment of a system configured to inspect a specimen. The system includes an illumination subsystem configured to illuminate specimen 10. The illumination subsystem includes light source 12. Light source 12 may be any suitable light source known in the art such as a laser light source. The systems described herein may, therefore, be configured for narrow band (NB) illumination and inspection. The light source may be configured to generate light having any suitable wavelength or wavelengths known in the art such as visible, ultraviolet (UV), deep ultraviolet (DUV), near vacuum ultraviolet (near-VUV), VUV, or some combination thereof. The wavelength(s) of the light generated by the light source may be selected based on, for example, one or more characteristics of the specimen, one or more characteristics of the defects of interest, and one or more characteristics of other optical components of the system.

The illumination subsystem may also include objective 14. Objective 14 may be configured to focus light generated by light source 12 onto specimen 10. In addition, as shown in FIG. 1, objective 14 is configured to direct the light to the specimen at an oblique angle of incidence. The oblique angle of incidence may include any suitable oblique angle of incidence known in the art. Objective 14 may include one refractive optical element as shown in FIG. 1. However, objective 14 may alternatively include one or more refractive optical elements and/or one or more reflective optical elements. In addition, objective 14 may include any suitable optical element(s) known in the art.

The illumination subsystem may also include any other suitable optical elements (not shown) known in the art. Examples of such optical elements include, but are not limited to, spectral filters, polarizing components, beam shaping elements, apertures, and any other optical elements known in the art.

The system also includes a collection subsystem configured to collect light scattered from specimen 10. In one embodiment, the collection subsystem includes lens 16 that is configured to collect light scattered from specimen 10. Lens 16 is also configured to collect light diffracted from periodic structures (not shown) on specimen 10. The periodic structures may include any periodic structures known in the art. Lens 16 may include an objective lens, a Fourier transform lens, or any other suitable optical element known in the art. In addition, although the collection subsystem is shown in FIG. 1 to include one lens, it is to be understood that the collection subsystem may include more than one optical element (one or more refractive optical elements and/or one or more reflective optical elements). Furthermore, the collection subsystem may include any other suitable optical element(s) (not shown) known in the art.

In one embodiment, the system shown in FIG. 1 also includes array 18 of micro-mirrors (not shown in FIG. 1) configured to reflect a two-dimensional pattern of light diffracted from the periodic structures on the specimen out of optical path 20 of the system without reflecting light across an entire dimension of the array out of the optical path. In one embodiment, array 18 is positioned at a Fourier plane of the collection subsystem. The micro-mirrors preferably extend across the entire optical path of the system. In this manner, array 18 may be used as a Fourier filter in the embodiments described herein. For example, as described further herein, the micro-mirror array may be used as a two-dimensional programmable Fourier filter in a flood illumination based dark field wafer inspection system. In addition, the micro-mirror array embodiments described herein may be used as two-dimensional programmable spatial light modulators (SLMs) in the illumination path and/or imaging path of an inspection system. For example, the micro-mirror array embodiments described herein may be used in an inspection system to alter the characteristics (e.g., shape, dimensions, pattern, etc.) of the area illuminated on a specimen by the system.

Reflecting light diffracted from periodic structures on the specimen out of the optical path of the system is advantageous for a number of reasons. For example, light diffracted from periodic structures on the specimen tends to be relatively bright in comparison to light scattered from defects on the specimen. Therefore, reflecting light diffracted from the periodic structures on the specimen out of the optical path of the system prevents the diffracted light from being detected (e.g., by a detection subsystem described further herein) thereby increasing the accuracy with which light scattered from defects can be detected. In addition, light diffracted from periodic structures tends to propagate in fairly predictable directions while light scattered from defects tends to scatter fairly randomly. Therefore, preventing light diffracted from the periodic structures on the specimen from being detected by reflecting the diffracted light out of the optical path of the system allows the light scattered from defects to be detected more easily.

Figure 2:
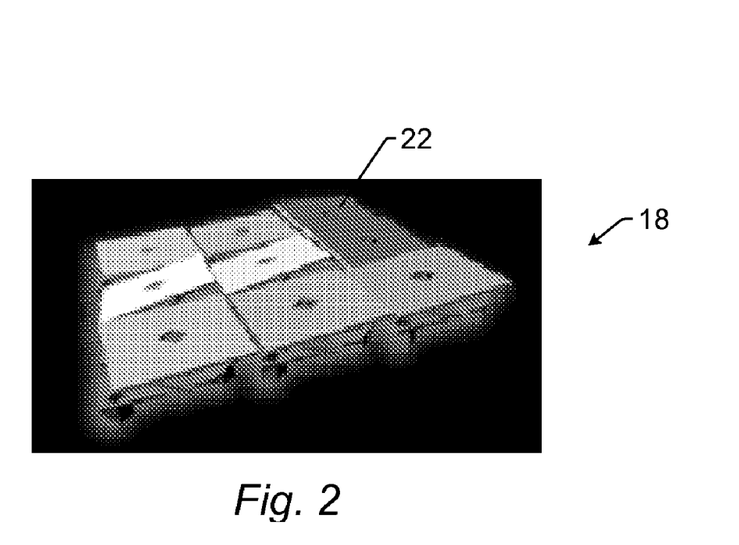
FIG. 2 is a schematic diagram illustrating a perspective view of one example of an array of micro-mirrors.

One example of an array of micro-mirrors that may be used in the embodiment shown in FIG. 1 is illustrated in FIG. 2. In this example, array 18 includes micro-mirrors 22. In addition, array 18 includes a two-dimensional array of micro-mirrors 22. This two-dimensional micro-mirror array may be placed in the Fourier plane of the system shown in FIG. 1 to block the diffraction energy from array structures formed on specimen 10. For example, as shown in FIG. 2, some of the micro-mirrors have different positions due to tilting of the micro-mirrors via the tilting mechanism. The position of each of the micro-mirrors determines the direction in which light will be reflected from each of the micro-mirrors.

In this manner, the positions of the micro-mirrors may be selected based on the micro-mirrors on which light diffracted from the periodic structures on the specimen will be incident. In particular, the positions of micro-mirrors on which light diffracted from the periodic structures on the specimen will be incident may be selected such that light reflected from these micro-mirrors is directed out of the optical path of the system. In addition, the positions of micro-mirrors on which light diffracted from the periodic structures will not be incident may be selected such that light reflected from these micro-mirrors is directed into the optical path of the system.

The positions of the individual micro-mirrors of the arrays described herein may be programmable (e.g., controllable by, for example, the system, a computer, processor, control subsystem, or control device (not shown)) such that the positions of the individual micro-mirrors of the array can be altered depending on the specimen being inspected by the system (e.g., based on the characteristics such as pitch and dimensions of the periodic structures or "array structures" formed on the specimen, which may be known a priori or based on prior experimentation). The array of micro-mirrors may, therefore, be configured as a programmable micro-mirror array. In this manner, a relatively large number of Fourier filtering patterns may be programmed onto one optical element. Examples of commercially available programmable mirror arrays include the Digital Micromirror Devices (DMD) that are commercially available from Texas Instruments Incorporated, Dallas, Tex.

Although the array of micro-mirrors shown in FIG. 2 includes a particular number of micro-mirrors, it is to be understood that an array included in the embodiments described herein may include any suitable number of micro-mirrors. In addition, although the micro-mirrors are shown in FIG. 2 as having a generally square shape, it is to be understood that the dimensions of the micro-mirrors may be selected as described further herein. The array shown in FIG. 2 may be further configured as described herein.

Figure 3:
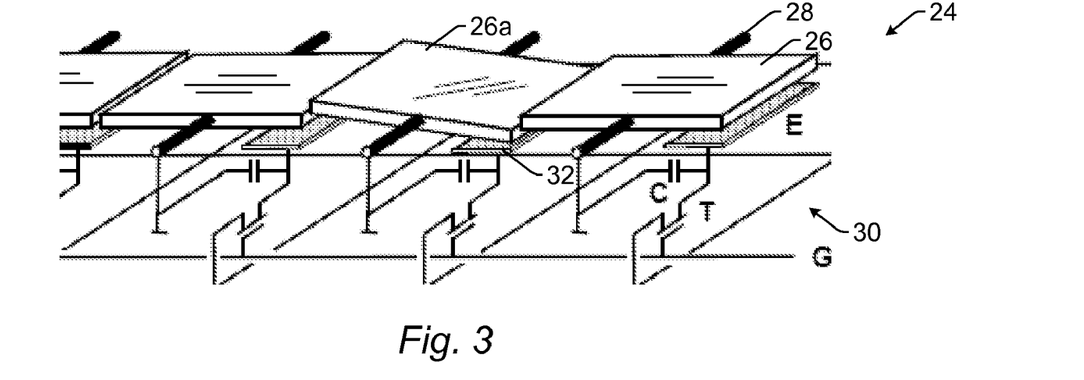
FIG. 3 is a schematic diagram illustrating a perspective view of one example of an array of micro-mirrors configured such that the micro-mirrors can be tilted.

In one embodiment, the array is configured such that the micro-mirrors can be independently tilted. For example, a tilt mechanism can be implemented with the array of micro-mirrors to "dump" the light received by a specific mirror out of the optical path of the system thereby making filtering possible. In another embodiment, the array is configured such that the micro-mirrors can be independently tilted based on the periodic structures formed on the specimen. In this manner, the micro-mirrors can be independently tilted based on the light diffracted from the periodic structures formed on the specimen. The tilting mechanism for each mirror may be controlled independently as described further herein. One example of an array of micro-mirrors configured such that the micro-mirrors can be tilted is shown in FIG. 3. Although the array of micro-mirrors is shown in FIG. 3 to include a one-dimensional array of micro-mirrors, the array may include a two-dimensional array of micro-mirrors as described further herein.

In this example, array 24 includes micro-mirrors 26. Each of the micro-mirrors is coupled to one of axes 28. In addition, the array includes circuitry 30 that is configured to alter a position of the micro-mirrors by causing the micro-mirrors to tilt about their axes 28. For example, circuitry includes electrodes E, and each of the micro-mirrors may be positioned above one of the electrodes. The circuitry may also include capacitors C, transistors T, and ground G, all of which in combination with the electrodes, may have any suitable configuration known in the art. Actuation of an electrode (e.g., by application or removal of a voltage to the electrode) causes the portion of the corresponding micro-mirror spaced above the electrode to move toward (and possibly contact) the electrode thereby causing tilting of the mirror about its axis. For example, as shown in FIG. 3, actuation of electrode 32 causes the portion of corresponding micro-mirror 26a spaced above the electrode to move toward electrode 32 causing tilting of the mirror about its axis. In this manner, the array of micro-mirrors may be configured as a plurality of microelectromechanical (MEMS) devices, each of which may be controlled by an appropriate subsystem (not shown).

Although the array is shown in FIG. 3 to include a tilting mechanism implemented as a MEMS device, it is to be understood that the arrays described herein may include any appropriate mechanism for altering the positions of the micro-mirrors. The array shown in FIG. 3 may be further configured as described herein.

Figure 4:
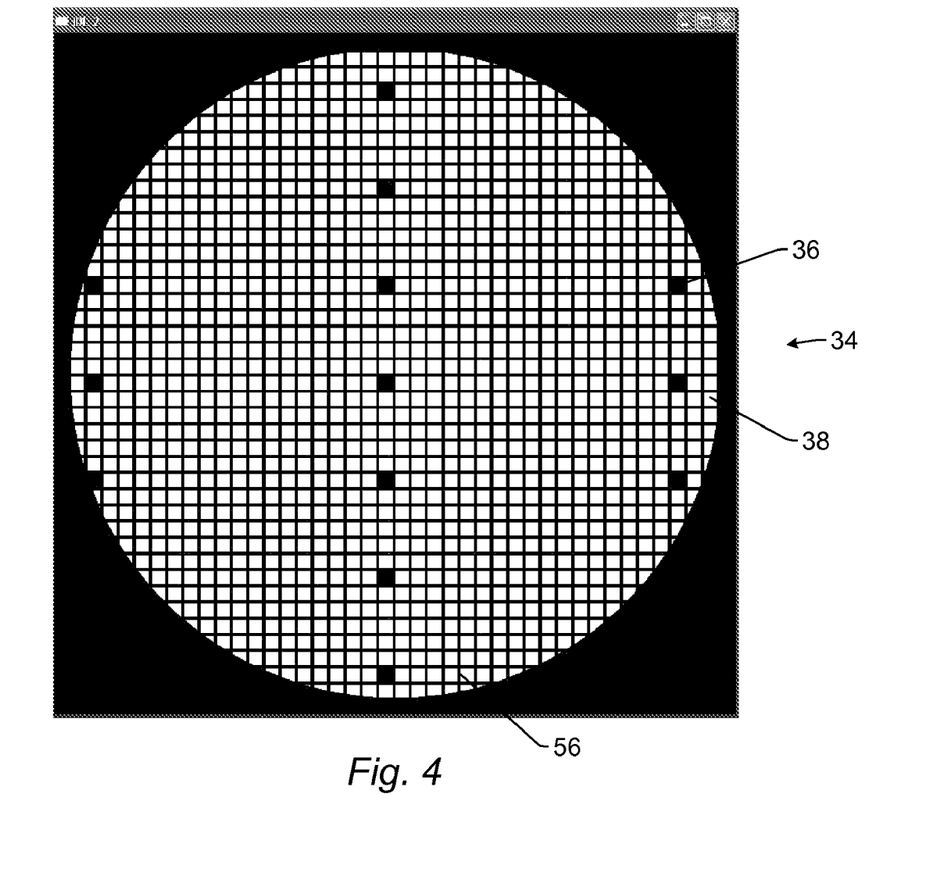
FIG. 4 is a schematic diagram illustrating a top view of one embodiment of an array of micro-mirrors configured to reflect a two-dimensional pattern of light diffracted from periodic structures on the specimen out of the optical path of a system without reflecting light across an entire dimension of the array out of the optical path.

FIG. 4 illustrates one embodiment of an array of micro-mirrors configured to reflect a two-dimensional pattern of light diffracted from periodic structures on a specimen out of the optical path of a system without reflecting light across an entire dimension of the array out of the optical path. In this embodiment, array 34 includes micro-mirrors 36 that are configured to "block" light by reflecting light incident thereon out of the optical path of the system and micro-mirrors 38 that are configured to reflect light into the optical path of the system. As described above, the array may be configured such that the micro-mirrors can be independently tilted. In this manner, micro-mirrors 36 are configured (e.g., tilted) such that these micro-mirrors reflect a two-dimensional pattern of light diffracted from periodic structures on the specimen out of the optical path of the system. In addition, micro-mirrors 38 are configured (e.g., not tilted) such that these micro-mirrors reflect light into the optical path of the system.

Micro-mirrors 36 are, therefore, arranged in a two-dimensional pattern within array 34 that is selected based on one or more characteristics (e.g., dimensions, pitch, etc.) of the periodic structures on the specimen. The two-dimensional pattern formed by micro-mirrors 36 may, therefore, correspond to a two-dimensional pattern formed in the Fourier plane by diffracted peaks of light collected by the collection subsystem. As such, the positions of the micro-mirrors may be independently selected and altered (e.g., by tilting) such that the two-dimensional array reflects a two-dimensional pattern of light diffracted from periodic structures on the specimen out of the optical path of the system.

Unlike some Fourier filters such as mechanical filters and previous implementations of Fourier filters, the array shown in FIG. 4 does not block light along an entire dimension of the Fourier filter. In other words, unlike previous Fourier filters that were only capable of or only used to block light one-dimensionally, the array embodiments described herein are capable of and are used to block light two-dimensionally. In this manner, the filter shown in FIG. 4 is configured and implemented such that the diffraction peaks in the light from the specimen can be blocked while allowing a larger amount of light to be detected. For example, the filter shown in FIG. 4 can reflect a larger amount of light scattered from defects on the specimen into the optical path of the system compared to mechanical filters and previous implementations of Fourier filters. As such, the filter shown in FIG. 4 can be used to provide a system that detects higher defect signals and therefore has higher defect detection sensitivity than other currently available systems. The embodiments of the arrays of micro-mirrors described herein are also advantageous since they are structurally sound and are suitable for use at DUV as well as other wavelengths. The array shown in FIG. 4 may be further configured as described herein.

The system shown in FIG. 1 also includes a detection subsystem configured to generate output responsive to light reflected by array 18 into optical path 20. The detection subsystem includes, in this embodiment, objective 40 and detector 42. Objective 40 is configured to image light reflected by array 18 into optical path 20 onto detector 42. Objective 40 may include, for example, any suitable imaging lens or focusing lens known in the art. In addition, although objective 40 is shown in FIG. 1 as one optical element, it is to be understood that objective 40 may include more than one optical element (one or more refractive optical elements and/or one or more reflective optical elements). Detector 42 may be any appropriate detector known in the art such as a charge coupled device (CCD) or time delay integration (TDI) camera. Detector 42 may be configured to generate output responsive to light reflected by array 18 into optical path 20. The detection subsystem may also include any other suitable optical element(s) (not shown) known in the art.

The output generated by the detection subsystem can be used to detect defects (not shown) on the specimen. For example, the system may include processor 44. Processor 44 may be coupled to detector 42 of the detection subsystem by a transmission medium (not shown). The transmission medium may include any suitable transmission medium known in the art. In addition, the processor may be coupled to the detector by one or more electronic components (not shown) such as an analog-to-digital converter. In this manner, processor 44 is configured to receive output from detector 42.

Processor 44 may be configured to use the output to detect defects on the specimen. The defects may include any defects of interest on the specimen. In addition, the processor may be configured to use the output and any method and/or algorithm known in the art to detect the defects on the specimen. Furthermore, processor 44 may be configured to perform any other inspection-related functions known in the art (e.g., defect location determination, defect classification, defect mapping, etc.).

Processor 44 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

In one embodiment, the system shown in FIG. 1 includes optical element 46 configured to increase the uniformity of the wavefront of the light reflected by array 18 into optical path 20. For example, optical element 46 may be configured as a corrector plate, or more specifically a phase corrector plate, positioned in front of the array. The corrector plate may be configured to preserve the wavefront of the system (to substantially prevent image degradation, which may otherwise be caused by, for example, non-uniformities in the wavefront caused by irregularities in the flatness of the individual micro-mirrors due to manufacturing limitations). The corrector plate may have any suitable configuration known in the art. In addition, although optical element 46 is shown in FIG. 1 as a refractive optical element, it is to be understood that the "corrector plate" may alternatively be configured as a reflective optical element.

The corrector plate may be manufactured using any suitable process known in the art. For example, one or more characteristics of the micro-mirror array such as flatness or any other characteristic(s) that may affect the wavefront of the light reflected by the array may be measured using a technique such as interferometry. Based on the measured characteristic(s) of the micro-mirror array, a corrector plate may be manufactured for the array using a process based on, for example, magnetorheological finishing (MRF) technology, which generally involves magnetically manipulating the viscosity of a fluid contacting a workpiece to create a subaperture polishing lap conforming to the optical surface of the workpiece to form high precision aspheres, spheres, and flats. In addition, the corrector plate may be manufactured using any commercially available MRF system. The system shown in FIG. 1 may be further configured as described herein. The system shown in FIG. 1 has all of the advantages of other embodiments described herein.

The illumination subsystem described above is also configured to illuminate a two-dimensional field of view (FOV) on the specimen. For example, the illumination subsystem may be configured to illuminate an area on the specimen that includes a relatively large number of pixels in two opposing directions (e.g., one hundred or more pixels by one hundred or more pixels). Such an illumination subsystem provides a type of illumination that may be commonly referred to as "flood illumination." In contrast to flood illumination, spot illumination used in spot scanning inspection systems commonly illuminates relatively few pixels on the specimen.

Figure 5:
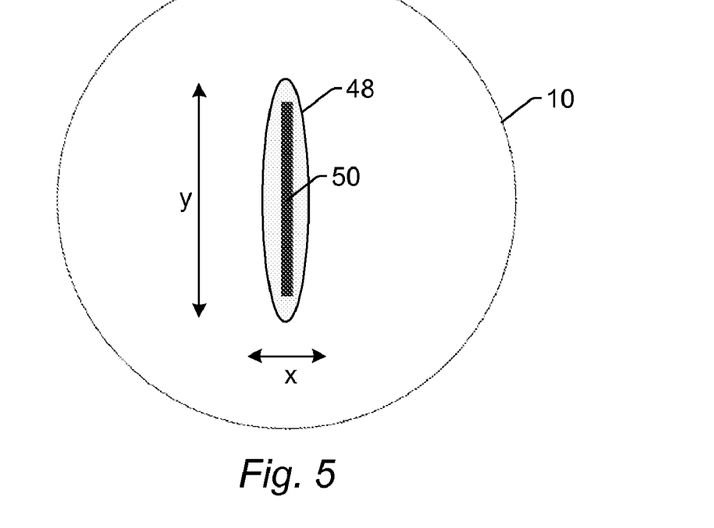
FIG. 5 is a schematic diagram illustrating a top view of one embodiment of a two-dimensional field of view (FOV) that may be illuminated on the specimen by a system embodiment described herein and a FOV of a detection subsystem of the system.

In one embodiment, the FOV has an approximately elliptical (or "oblong") shape on the specimen. For example, as shown in FIG. 5, FOV 48 has an approximately elliptical shape on specimen 10. Such a shape of the FOV may be caused by the angle of incidence at which the illumination subsystem directs light to the specimen. For example, a light beam that has a substantially circular cross-section may appear to have a substantially elliptical cross-section when projected onto the specimen at an oblique angle of incidence. As further shown in FIG. 5, light scattered from FOV 48 on specimen 10 may be imaged onto detector 50, which is shown in FIG. 5 superimposed on FOV 48 to illustrate the similarities in the shapes of the FOV and the detector. For example, as shown in FIG. 5, the shapes of the FOV and the detector are relatively similar such that a substantial portion of the pixels in the FOV on the specimen can be imaged onto pixels of the detector. In one embodiment, detector 50 may be a TDI camera that has a two-dimensional array of pixels. In one such embodiment, the TDI camera may include about 400 pixels along one dimension of the TDI camera and about 4000 pixels along the opposite dimension.

As further shown in FIG. 5, therefore, FOV 48 may have dramatically different dimensions in the y direction and the x direction. As shown in FIG. 5, for purposes of discussion herein, the long FOV axis (e.g., the major axis) is defined as the y axis that extends in the y direction, and the short FOV axis (e.g., the minor axis) is defined as the x axis that extends in the x direction. The x and y directions are referenced to the specimen plane, and scanning of the FOV across the specimen may be performed in the x direction. Therefore, in one embodiment, a dimension of FOV 48 in the y direction is larger than a dimension of the FOV in the x direction. Such characteristics of the FOV may be advantageously used to select a configuration for the array shown in FIG. 1.

In one embodiment, if a dimension of FOV 48 in the y direction is larger than a dimension of the FOV in the x direction, a dimension of the micro-mirrors parallel to the y direction is larger than a dimension of the micro-mirrors parallel to the x direction. In this manner, the dimensions of the micro-mirrors can be selected to have about the same relationship to each other (e.g., ratio) as the dimensions of the FOV have to each other.

Figure 6:
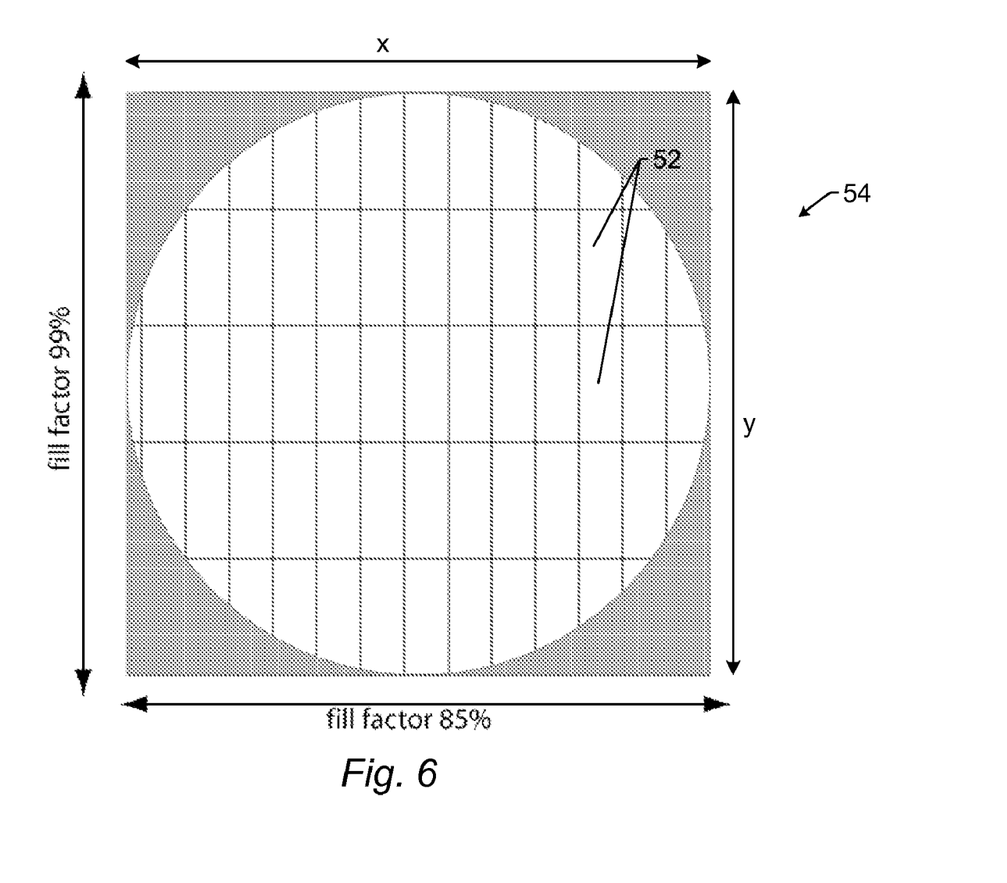
FIG. 6 is a schematic diagram illustrating a top view of one embodiment of an array of mirrors that may be included in a system embodiment described herein.

One embodiment of such an array of micro-mirrors is shown in FIG. 6. As shown in FIG. 6, individual micro-mirrors 52 of array 54 have a rectangular shape (unlike the square shape of micro-mirrors of currently used arrays) since the dimension of the individual micro-mirrors in the x direction, which corresponds to the x direction shown in FIG. 5, is smaller than the dimension of the individual micro-mirrors in the y direction, which corresponds to the y direction shown in FIG. 5. In one example, the dimension of each micro-mirror in the x direction may be about 20 μm, and the dimension of each micro-mirror in the y direction may be about 400 μm. The dimensions of the micro-mirrors in the x and y directions may vary, however, depending on, for example, the dimensions of the FOV on the specimen and the FOV of the detection subsystem.

Due to the different dimensions of the micro-mirrors in the different directions, the micro-mirror array will have different fill factors in the x and y directions. For example, based on the examples of the dimensions described above, the array may have a fill factor of about 90% in the x direction, and a fill factor of about 99.5% in the y direction. In one embodiment, therefore, a dimension of the FOV in a y direction is larger than a dimension of the FOV in an x direction, and a fill factor of the micro-mirrors parallel to the y direction is larger than a fill factor of the micro-mirrors in the x direction.

In one embodiment, an array of micro-mirrors having the dimensions described according to the above embodiments is configured such that the micro-mirrors are tilted in the x direction. For example, since the micro-mirrors shown in FIG. 6 have smaller dimensions in the x direction than the y direction, the tilt scheme for the array may be to tilt the individual micro-mirrors in the x direction, which results in a lower maximum tilt angle for each individual micro-mirror and a lower maximum tilt displacement for each individual micro-mirror than if the micro-mirrors are tilted in the y direction. For example, tilting the micro-mirrors, shown in FIG. 6 having the dimensions described in the example above, in the x direction may result in a maximum tilt angle of about 12 degrees and a maximum tilt displacement of about 2.12 μm.

One concern when selecting a configuration of a Fourier filter such as an array of micro-mirrors described herein is the dead space of the array and the Fourier filter blockage of the array, which are the main parameters that can cause ringing and/or periphery leakage in the output of the system. In a preferred embodiment, the array is configured to reflect approximately all ringing energy due to dead space in the array outside of the FOV of the detection subsystem. For example, in one embodiment, a dimension of the FOV illuminated on the specimen in a y direction is larger than a dimension of the FOV in an x direction. In one such embodiment, a dimension of the micro-mirrors parallel to the y direction is larger than a dimension of the micro-mirrors parallel to the x direction, and the dimension of the micro-mirrors in the x direction is selected such that the array reflects approximately all dead space ringing energy outside of the FOV of the detection subsystem in the x direction.

In particular, the distance between diffraction locations due to the dead space is inversely proportional to the pitch of the dead space. In this manner, as the pitch of the dead space increases (and therefore the dimensions of the micro-mirrors increase), the distance between diffraction locations due to the dead space decreases. For example, distance, L, between diffraction locations is related to pitch, d, of the dead space according to the following equation: $L=\lambda/d$, where $\lambda$ is the illumination wavelength. Therefore, in embodiments described herein, L may be selected to be larger than the FOV of the detection subsystem in the x direction, and the pitch of the dead space in the x direction in the array may be determined according to the above equation. Therefore, the dimension of the micro-mirrors in the x direction can be determined based on the determined pitch of the dead space in the x direction. In some embodiments, therefore, the array is configured such that the array does not cause degradation of the output generated by the detection subsystem. In addition, the dimensions of the individual micro-mirrors in both directions may be selected (and possibly optimized) such that degradation of the output is reduced (and possibly minimized).

Figure 7:
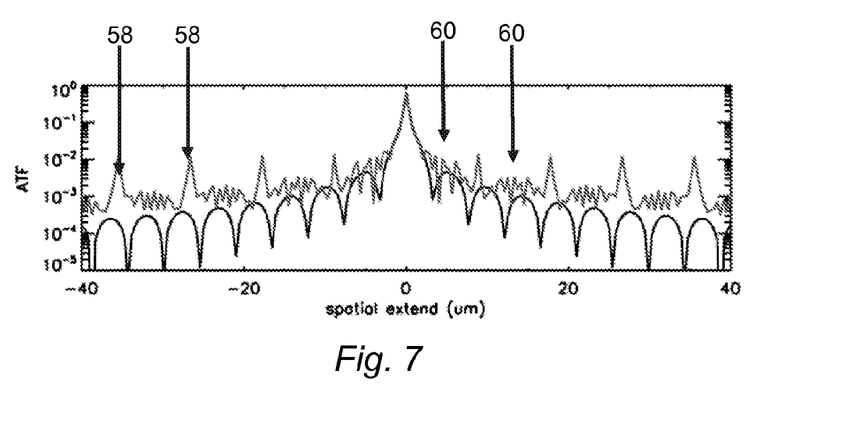
FIG. 7 is a plot illustrating ringing and leakage caused by the array of micro-mirrors shown in FIG. 4.
Figure 8:
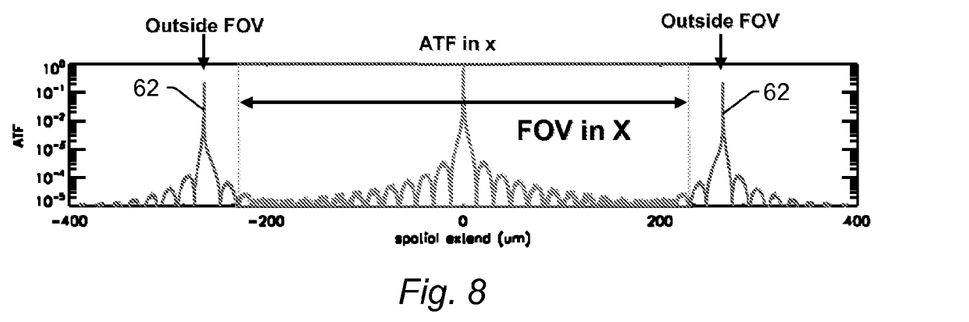
FIG. 8 is a plot illustrating ringing in the x direction of the FOV of a detection subsystem due to dead space in the array shown in FIG. 6.
Figure 9:
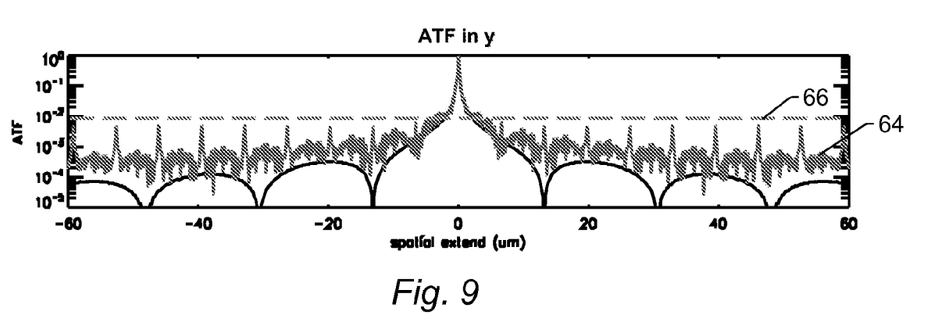
FIG. 9 is a plot illustrating leakage in the y direction of the FOV of a detection subsystem due to diffraction from the micro-mirrors of the array shown in FIG. 6.

FIGS. 7-9 illustrate the differences between the performance of different micro-mirror arrays. For instance, FIG. 7 illustrates simulation results for the ATF as a function of spatial extent for the micro-mirror array shown in FIG. 4, a cell size of about 0.5 μm×about 1.5 μm, and an assumed dead space width of about 2 μm. As shown in FIG. 4, dead space 56 of the array is the space between the individual micro-mirrors of the array. This array is configured to have a relatively low fill factor, which is suitable for relatively high pixel resolution. However, as shown in FIG. 7, the array causes significant ringing 58 due to dead spaces 56 of the array. In addition, the array causes leakage 60 due to Fourier filter blockage. However, as shown in FIG. 7, the dominant ringing or leakage comes from the dead space of the array. In contrast, in a relatively high fill factor, relatively low pixel resolution array (not shown), Fourier filtering may dominate the ringing and/or leakage. Therefore, the optimal micro-mirror dimensions may be dimensions that are neither too large nor too small such that the leakage is not dominated by either the fill factor (i.e., dead space) or the Fourier filters.

In contrast to the performance of the array shown in FIG. 4, the array shown in FIG. 6 exhibits significantly different ringing and leakage. For example, FIG. 8 illustrates simulation results for the ATF of the array shown in FIG. 6 as a function of spatial extent in the x direction, which may be defined as described above, of the FOV of the detection subsystem. In addition, FIG. 9 illustrates simulation results for the ATF of the array shown in FIG. 6 as a function of spatial extent in the y direction, which may be defined as described above, of the FOV of the detection subsystem. As shown in FIG. 8, ringing 62 caused by the array in the x direction due to dead spaces of the array falls outside of the FOV of the detector. In particular, ringing 62 caused by the array in the x direction due to the dead spaces of the array falls outside of the FOV of the detector because the dimensions of the micro-mirrors in this direction are relatively small. In addition, as shown in FIG. 9, leakage 64 caused by the array in the y direction due to Fourier filter blockage is below noise floor 66 of the detection subsystem. In this manner, the ringing and leakage caused by the array shown in FIG. 6 will not cause degradation of the output generated by the detection subsystem.

Such a configuration of the array of micro-mirrors has a number of advantages over using other configurations of arrays of micro-mirrors in the embodiments of the systems described herein. For instance, one difficulty of using a micro-mirror array as a Fourier filter is to ensure that the ringing effect caused by the dead space of the array is well below the noise floor. To do so, the micro-mirror array requires an extremely high fill factor thereby rendering the micro-mirror array not likely to be manufacturable (e.g., due to the performance required of the etch process used to fabricate the micro-mirror array). The embodiments described herein take advantage of the fact that the most cost-effective and efficient flood illumination scheme for dark field flood illumination based systems uses an elliptical shaped illumination pattern with one axis of the FOV much larger than the other axis. Under such an illumination scheme, a micro-mirror array that includes micro-mirrors having a substantially small dimension in the x direction can "push" substantially all of the dead space ringing energy outside of the FOV of the detection subsystem in the x direction. Therefore, the embodiments described herein allow true two-dimensional programmable Fourier filtering for a flood illumination based system without significant image degradation and dead space ringing leakage. Such a configuration lowers the overall fill factor criteria thereby rendering the micro-mirror array manufacturable.

In one preferred embodiment, the corrector plate described above is used in combination with the rectangular micro-mirrors described above. For example, in one embodiment, the system shown in FIG. 1 includes optical element 46 configured to increase the uniformity of the wavefront of the light reflected by array 18 into optical path 20. In one such embodiment, a dimension of the FOV (not shown in FIG. 1) on specimen 10 illuminated by the illumination subsystem in a y direction is larger than a dimension of the FOV in an x direction. The x and y directions may be defined as described above. In addition, the FOV may be configured as described above. In such an embodiment, a dimension of the micro-mirrors (not shown in FIG. 1) of array 18 parallel to the y direction is larger than a dimension of the micro-mirrors parallel to the x direction. In this manner, the corrector plate technology described above may be combined with the micro-mirror technology described above to construct a programmable two-dimensional Fourier filter for a flood illumination based system. Such an embodiment may be further configured as described herein and has all of the advantages described herein.

According to one embodiment, a system configured to inspect a specimen includes a collection subsystem configured to collect light scattered from the specimen. The collection subsystem may be configured as described herein and shown in FIG. 1. The system also includes an array of micro-mirrors configured to reflect light diffracted from periodic structures on the specimen out of the optical path of the system. The array of micro-mirrors may be configured as described herein and shown in the figures described herein. In addition, the system includes an optical element configured to increase the uniformity of the wavefront of light reflected by the array into the optical path of the system. The optical element may be configured as described herein and shown in FIG. 1. The system further includes a detection subsystem configured to generate output responsive to light exiting the optical element. The output can be used to detect defects on the specimen. The detection subsystem may be configured as described herein and shown in FIG. 1. In addition, the output may be used to detect defects on the specimen as described herein.

In one embodiment, a dimension of the FOV of the system in a y direction is larger than a dimension of the FOV in an x direction. The FOV may be configured as described herein and shown in FIG. 5. In one such embodiment, a dimension of the micro-mirrors parallel to the y direction is larger than a dimension of the micro-mirrors parallel to the x direction. This embodiment of the array of micro-mirrors may be configured as described herein and shown in FIG. 6. In another embodiment, the array is configured to reflect approximately all ringing energy due to dead space in the array outside of the FOV of the detection subsystem. Such an embodiment of the array may be configured as described herein. In a further embodiment, the array is configured such that the array does not cause degradation of the output. Such an embodiment of the array may also be configured as described herein. Each of the embodiments of the system described above may be further configured as described herein. In addition, each of the embodiments of the system described above has all of the advantages of other embodiments described herein.

According to another embodiment, a system configured to inspect a specimen includes an illumination subsystem configured to illuminate a two-dimensional FOV on the specimen. The illumination subsystem may be configured as described herein and shown in FIG. 1. A dimension of the FOV in a y direction is larger than a dimension of the FOV in an x direction. The FOV may be configured as described herein and shown in FIG. 5. The system also includes a collection subsystem configured to collect light scattered from the specimen. The collection subsystem may be configured as described herein and shown in FIG. 1. In addition, the system includes an array of micro-mirrors configured to reflect light diffracted from periodic structures on the specimen out of the optical path of the system. A dimension of the micro-mirrors parallel to the y direction is larger than a dimension of the micro-mirrors parallel to the x direction. The array of micro-mirrors may be configured as described herein and shown in FIGS. 1 and 6. The system further includes a detection subsystem configured to generate output responsive to light reflected by the array into the optical path.

The output can be used to detect defects on the specimen. The detection subsystem may be configured as described herein and shown in FIG. 1. In addition, the output may be used to detect defects on the specimen as described herein.

In one embodiment, a fill factor of the micro-mirrors parallel to the y direction is larger than a fill factor of the micro-mirrors parallel to the x direction. Such an embodiment of the array may be configured as described herein and shown in FIG. 6. In another embodiment, the array is configured such that the micro-mirrors are tilted in the x direction. Such an embodiment of the array may be further configured as described herein. In an additional embodiment, the array is configured to reflect approximately all ringing energy due to dead space in the array outside of the FOV of the detection subsystem. This embodiment of the array may be further configured as described herein. In a further embodiment, the array is configured such that the array does not cause degradation of the output. This embodiment of the array may be configured as described herein. Each of the embodiments of the system described above may be further configured as described herein. In addition, each of the embodiments of the system described above has all of the advantages of other embodiments described herein.

It is noted that the figures are provided herein to generally illustrate various configurations of embodiments of a system configured to inspect a specimen. Obviously, the system configurations described herein may be altered to optimize the performance of the system as is normally performed when designing a commercial inspection system. In addition, the systems described herein may be implemented using an existing inspection system (e.g., by inserting an array of micro-mirrors and a corrector plate described herein in an existing inspection system such as one of the Puma 9000 Series tools that are commercially available from KLA-Tencor, San Jose, Calif.). For some such systems, the inspection functionality described herein may be provided as optional functionality of the system (e.g., in addition to other functionality of the system). Alternatively, the systems described herein may be designed "from scratch" to provide a completely new system.

Further modifications and alternative embodiments of various aspects of the invention may be apparent to those skilled in the art in view of this description. For example, systems configured to inspect a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a specimen, comprising:
    an illumination subsystem configured to illuminate a two-dimensional field of view on the specimen, wherein a dimension of the field of view in a y direction is larger than a dimension of the field of view in an x direction;
    a collection subsystem configured to collect light scattered from the specimen;
    an array of micro-mirrors configured to reflect a two-dimensional pattern of light diffracted from periodic structures on the specimen out of the optical path of the system without reflecting light across an entire dimension of the array out of the optical path, wherein a dimension of the micro-mirrors parallel to the y direction is larger than a dimension of the micro-mirrors parallel to the x direction; and
    a detection subsystem configured to generate output responsive to light reflected by the array into the optical path, wherein the output is used to detect defects on the specimen.

2. The system of claim 1, wherein the array is positioned at a Fourier plane of the collection subsystem.

3. The system of claim 1, further comprising an optical element configured to increase the uniformity of the wavefront of the light reflected by the array into the optical path.

4. The system of claim 1, wherein the field of view has an approximately elliptical shape on the specimen.

5. The system of claim 1, wherein a fill factor of the micro-mirrors parallel to the y direction is larger than a fill factor of the micro-mirrors parallel to the x direction.

6. The system of claim 1, wherein the array is further configured such that the micro-mirrors are tilted in the x direction.

7. The system of claim 1, wherein the array is further configured to reflect approximately all ringing energy due to dead space in the array outside of the field of view of the detection subsystem.

8. The system of claim 1, wherein the dimension of the micro-mirrors in the x direction is selected such that the array reflects approximately all dead space ringing energy outside of the field of view of the detection subsystem in the x direction.

9. The system of claim 1, wherein the array is further configured such that the array does not cause degradation of the output.

10. The system of claim 1, wherein the array is further configured such that the micro-mirrors can be independently tilted.

11. The system of claim 1, wherein the array is further configured such that the micro-mirrors can be independently tilted based on the periodic structures formed on the specimen.

12. A system configured to inspect a specimen, comprising:
    a collection subsystem configured to collect light scattered from the specimen;
    an array of micro-mirrors configured to reflect light diffracted from periodic structures on the specimen out of the optical path of the system;
    an optical element configured to increase the uniformity of the wavefront of light reflected by the array into the optical path of the system; and
    a detection subsystem configured to generate output responsive to light exiting the optical element, wherein the output is used to detect defects on the specimen;
    wherein a dimension of the field of view of the system in a y direction is larger than a dimension of the field of view in an x direction and wherein a dimension of the micro-mirrors parallel to the y direction is larger than a dimension of the micro-mirrors parallel to the x direction.

13. The system of claim 12, wherein the array is further configured to reflect approximately all ringing energy due to dead space in the array outside of the field of view of the detection subsystem.

14. The system of claim 12, wherein the array is further configured such that the array does not cause degradation of the output.

15. A system configured to inspect a specimen, comprising:
- an illumination subsystem configured to illuminate a two-dimensional field of view on the specimen, wherein a dimension of the field of view in a y direction is larger than a dimension of the field of view in an x direction;
- a collection subsystem configured to collect light scattered from the specimen;
- an array of micro-mirrors configured to reflect light diffracted from periodic structures on the specimen out of the optical path of the system, wherein a dimension of the micro-mirrors parallel to the y direction is larger than a dimension of the micro-mirrors parallel to the x direction; and
- a detection subsystem configured to generate output responsive to light reflected by the array into the optical path, wherein the output is used to detect defects on the specimen.

16. The system of claim 15, wherein a fill factor of the micro-mirrors parallel to the y direction is larger than a fill factor of the micro-mirrors parallel to the x direction.

17. The system of claim 15, wherein the array is further configured such that the micro-mirrors are tilted in the x direction.

18. The system of claim 15, wherein the array is further configured to reflect approximately all ringing energy due to dead space in the array outside of the field of view of the detection subsystem.

19. The system of claim 15, wherein the array is further configured such that the array does not cause degradation of the output.

* * * * *